United States Patent
Gilmore

(10) Patent No.: US 7,344,047 B2
(45) Date of Patent: *Mar. 18, 2008

(54) AUTOMATIC MEDICAMENT DISPENSER SYSTEM

(75) Inventor: Janice F. Gilmore, Greer, SC (US)

(73) Assignee: Handy-I Med Solutions, LLC, Greer, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/962,210

(22) Filed: Oct. 8, 2004

(65) Prior Publication Data

US 2005/0209733 A1    Sep. 22, 2005

Related U.S. Application Data

(63) Continuation of application No. 10/308,910, filed on Dec. 2, 2002, now abandoned, which is a continuation-in-part of application No. 10/078,691, filed on Feb. 19, 2002, now abandoned, which is a continuation of application No. 09/702,554, filed on Oct. 31, 2000, now abandoned, which is a continuation of application No. 09/101,045, filed on Jun. 25, 1998, now Pat. No. 6,138,865.

(51) Int. Cl.
*G07F 11/00* (2006.01)

(52) U.S. Cl. .................. 221/2; 221/7; 221/13; 221/69

(58) Field of Classification Search .................. 221/2, 221/3, 7, 13, 69; 700/242, 235
See application file for complete search history.

(56) References Cited

U.S. PATENT DOCUMENTS 3,057,473 A    10/1962    Stern et al.
3,143,207 A    8/1964     Wagner
3,651,984 A    3/1972     Redenbach
3,871,551 A    3/1975     Bender
3,917,045 A    11/1975    Williams et al.
4,126,247 A    11/1978    Majka
4,223,801 A    9/1980     Carlson
4,267,942 A    5/1981     Wick, Jr. et al.
4,473,884 A    9/1984     Behl
4,572,403 A    2/1986     Benaroya
4,663,621 A    5/1987     Field et al.
4,664,289 A    5/1987     Shimizu et al.
4,717,042 A    1/1988     McLaughlin
4,733,362 A    3/1988     Haraguchi
4,811,764 A    3/1989     McLaughlin (Continued)

FOREIGN PATENT DOCUMENTS

WO    WO 9724702    7/1997

*Primary Examiner*—David H Bollinger
(74) *Attorney, Agent, or Firm*—Nelson Mullins Riley & Scarborough LLP

(57) ABSTRACT

A mobile medicine storage unit for individuals under a doctor's care. The unit is programmable and preferably fully automatic, but also manual, in dispensing any number of medications up to four times per day at preselected times. Audible and visible indicators alert patients of proper dosages and timings of these doses. An optional integral water reservoir and cup dispenser makes it possible to properly take all medications with minimal effort at the unit. Patients not in close proximity to the unit will be alerted remotely via a pager. The unit will contact programmable emergency phone numbers when no patient response is received. Programmability allows customizing to accommodate individual medication needs. Mobility is aided by an optional wheeled cart.

14 Claims, 12 Drawing Sheets

U.S. PATENT DOCUMENTS

| | | |
|---|---|---|
| 4,831,562 A | 5/1989 | McIntosh et al. |
| 4,911,327 A | 3/1990 | Shepherd et al. |
| 5,029,726 A | 7/1991 | Pendill |
| 5,099,463 A | 3/1992 | Lloyd et al. |
| 5,200,891 A | 4/1993 | Kehr et al. |
| 5,292,029 A | 3/1994 | Pearson |
| 5,314,243 A | 5/1994 | McDonald et al. |
| 6,138,865 A * | 10/2000 | Gilmore ............ 221/2 |

* cited by examiner

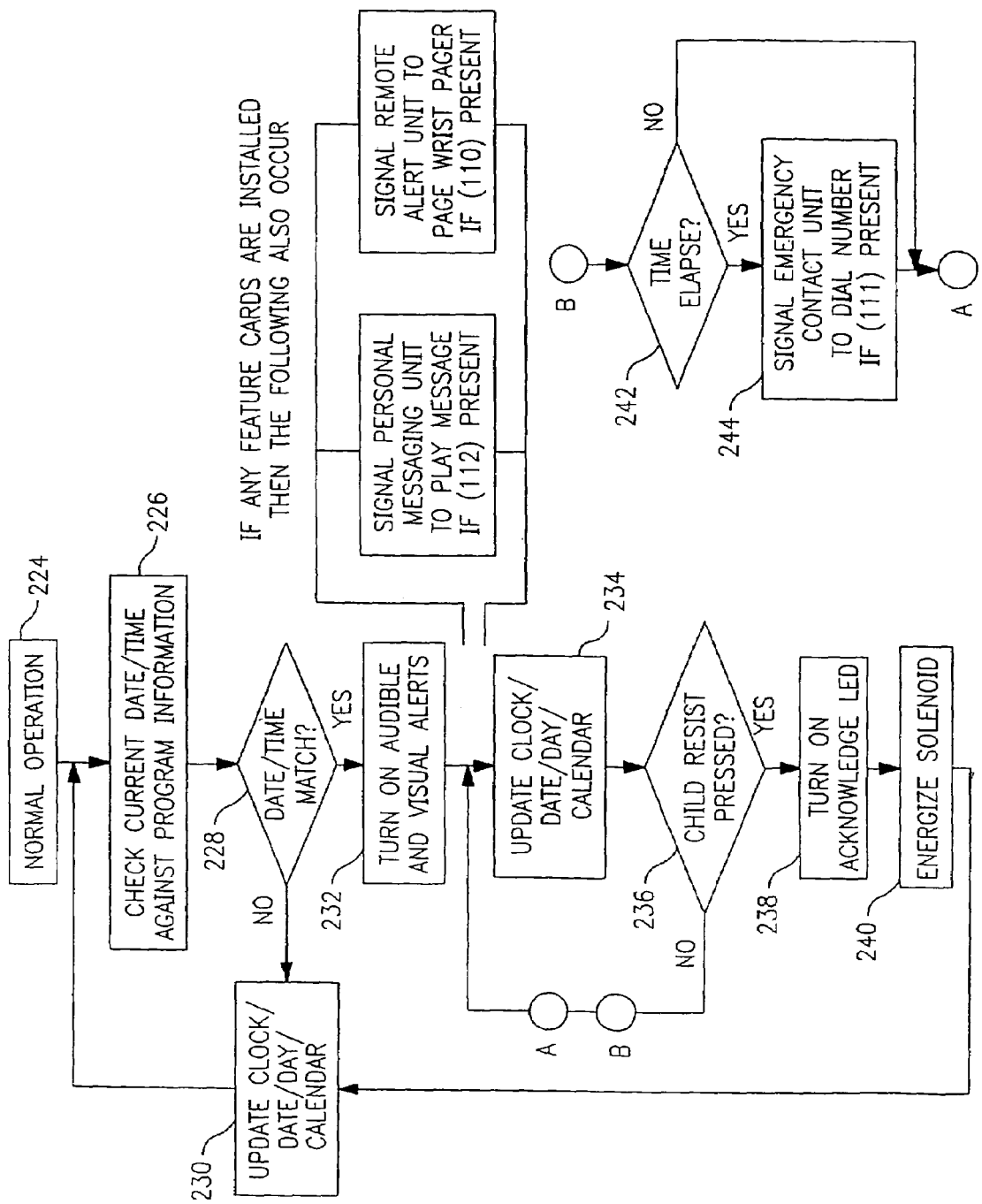

AUTOMATIC MEDICAMENT DISPENSER SYSTEM

CROSS-REFERENCE TO RELATED APPLICATIONS

This application is a continuation of application Ser. No. 10/308,910, filed Dec. 2, 2002 now abandoned, which was a continuation-in-part of applicant's application Ser. No. 10/078,691, filed Feb. 19, 2002, now abandoned, which was a continuation of application Ser. No. 09/702,554, filed Oct. 31, 2000 now abandoned, which was a continuation of application Ser. No. 09/101,045, now U.S. Pat. No. 6,138,865, which was based on application PCT/US96/20846, filed Dec. 27, 1996, which was based on provisional application Ser. No. 60/009,395, filed Dec. 29, 1995.

BACKGROUND OF THE INVENTION

The present invention relates to an improved system for dispensing and delivering medicaments. In particular, the invention relates to such a system that is friendly, convenient, facilitates orientation of the patient, and serves as a "virtual" companion in the absence of a human caregiver.

The rapidly changing global demographic make-up in regard to population increase of elderly people is putting great strains on the health care system. For example, the increase in elderly population has produced a proportionate increase in the full-time use of certain health care resources, such as hospital beds and nursing home beds. In addition, the need for constant supervision by nurses and other caretakers is increasing.

One way to ease this burden is to allow those in need of care to be more self-reliant. For example, medicament dispensers can be utilized to store and dispense medication to the patient at predetermined times. Many such devices have been proposed in the prior art. In general, these devices have lacked the combination of features to virtually replace the attention of a human caregiver.

When taking dosages of medication, it is extremely important that the dosages be taken on time and in the prescribed amounts. When it is time to take the medication, the user should not be concerned with having water and a cup so that the medicaments can be properly swallowed.

SUMMARY OF THE INVENTION

The present invention recognizes and addresses various disadvantages of prior art constructions and methods. Accordingly, it is an object of the present invention to provide an improved medicament dispenser system.

It is a more particular object of the present invention to provide an automatic medicament dispenser system that can largely replace the attention of a human caregiver.

It is a further object of the present invention to provide an automatic medicament dispenser system that orients the patient.

It is a further object of the present invention to provide an automatic medicament dispenser system that prevents unauthorized access to the medication, such as by children.

This invention provides a precise means of dispensing medicaments to persons (who may or may not be mentally impaired) under a doctor's care without the necessity of a caregiver being present. In its various aspects, the invention includes a broad range of features, such as a novel calendar layout and means to ensure access to the medication is virtually child proof.

One preferred embodiment of the invention consists of five rows of seven modules. The seven modules represent each day of the week and the five rows provide enough compartments to hold medicaments for a full month. Each of the seven modules may have four compartments which open individually, upon command from the microprocessor, thus dispensing up to four doses of pre-loaded medicaments each twenty-four hour period.

It is the intention of this unit to be fully programmable. Preferably, the unit is microprocessor driven in order to simplify programming and enhance safety, convenience and feature capabilities. The compartments may be programmed by the microprocessor to open at any particular time, once per day. A "locked" keypad is provided to program the unit for individual needs.

Once programmed, the unit may be fully automatic and only monthly refills of medicaments are required. This eliminates the need for a caregiver to measure the medicine precisely over an extended period of time. A latch-key mechanism allows authorized key holders to have easy access to all compartments. A medicine data sheet may be provided as a reference to indicate the medication to be loaded into the unit as well as providing other important information.

Preferably, the compartments will have fully automatic opening capabilities. In conjunction with a dispensing actuator, the lids lift automatically, revealing the medicaments, at preprogrammed times. While the dispensing actuator may be a simple button, presently preferred embodiments of the invention utilize a user-specific actuator to make the unit virtually child-proof, as well as to prevent unauthorized adults from gaining access to the medication. Presently preferred embodiments utilize a finger print reader for this purpose, although other suitable technologies may be utilized for this purpose as set forth below.

In a presently preferred construction, the unit may have a total of thirty-five (35) compartments (or thirty-two (32) in some constructions with water present). Each of the compartments may be equipped with a digital display representing the date and day of the month. The date and day may light up as the month proceeds to enhance orientation of the user. A Braille representation of the day may also be provided for those users who are visually impaired. Strips having the Braille representations could be added into plate slots inserted by a pharmacist.

The date displays preferably change automatically, month to month, without any additional programming intervention. A digital display on the control panel of the device may display time in a twelve-hour format with A.M. and P.M. indicators. Another display on the control panel may display the current month in a three letter format and the current date. Again, all displays are preferably fully automatic in representing the current date and time and require no user intervention to maintain accuracy. A battery backup may be utilized to maintain accuracy in the event of a power failure.

To ensure the user receives medicine at the proper time, an audible alarm and/or a visible alarm are preferably provided. These alarms are issued when the current time, month, and date match their pre-programmed values, thus alerting the user to the need for medication.

To further simplify the taking of medicines and to ensure they are taken properly, an optional built-in water reservoir and dispensing pump, and a disposable-cup holder, may be provided at the unit for taking medications which require liquids. For convenience in placing the unit in strategic locations, an optional wheeled cart may be provided. Preferably, the wheels can be locked when the unit is at the desired location to maintain stability. In some embodiments, the cart can be motorized and a remote control device can be provided to facilitate movement of the cart.

An enhanced embodiment may also be provided which offers several extra capabilities to provide for further safety and convenience. One such capability is a wrist-worn pager. This allows the user to maintain freedom of mobility, while still being alerted to the need for taking medication. A paging (remote alert) unit is inserted into the control panel under the control of the microprocessor. The user wears the pager on his or her wrist that receives signals from the paging unit. In this manner, the pager will vibrate and sound an audible alarm when the microprocessor determines that medication is to be taken.

Another such capability is an emergency alert unit. This unit may also be inserted into the control panel and connected to the microprocessor. This unit will be programmed by the microprocessor. If the patient does not respond in a certain length of time to the unit's alarms (as determined by the unit's programming), an emergency-contact phone number is dialed. The dialing will continue until a contact is reached, at which time an emergency message is played, thus alerting a concerned individual of a possible problem with the patient.

Another advantageous capability may be obtained by adding a personal-voice massaging unit. This unit can be inserted into the control panel and controlled by the microprocessor. Whenever an audible alert is called for, this unit will allow a pre-recorded voice message to play. This voice may preferably be a familiar voice, such as that of a close relative.

Some embodiments of the invention include means for providing monitoring from the unit or two-way communication with a control monitoring facility. For example, the unit may include a video monitor and a video camera. If the patient has not used the dispensing actuator in a predetermined period after medicine is due, the central monitoring facility can be alerted.

The dispensing unit of the present invention preferably has various indicia and other features that facilitate, orientation of the patient. In accordance with medical understanding, an individual is considered to be "oriented" if aware of time, date, place and person. The dispensing unit aids in this orientation, thus contributing to the peace of mind of the patient and caregiver.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

FIG. 14 is a flow chart of preferred logic utilized in the microprocessor during normal operation.

Figure 1:
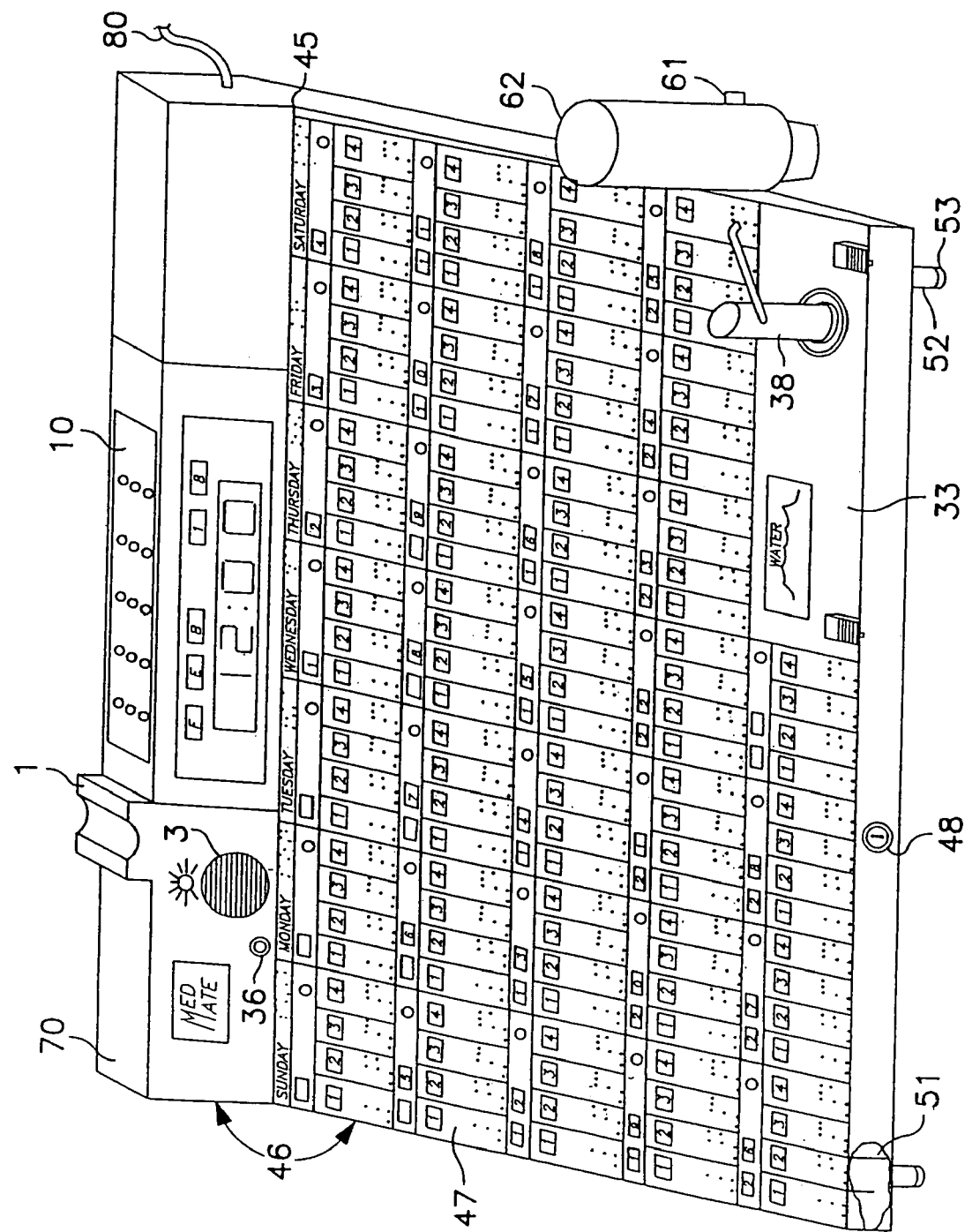
FIG. 1 is a perspective view of a medication dispenser constructed according to the invention, with cover closed.

Repeat use of reference characters in the present specification and drawings is intended to represent same or analogous features or elements of the invention.

DETAILED DESCRIPTION OF PREFERRED EMBODIMENTS

It is to be understood by one of ordinary skill in the art that the discussion herein is a description of exemplary embodiments only, and is not intended as limiting the broader aspects of the present invention, which broader aspects are embodied in the exemplary constructions.

FIG. 1 illustrates a programmable medication dispensing unit in a calendar format constructed in accordance with the present invention. The medication dispensing unit preferably comprises a perpetual calendar, controlled by electronic logic, which dispenses medicine using four compartments per day automatically.

The microprocessor employed by the medication dispenser reminds the patient to take a certain medication in a manner that is highly accurate, yet flexible should a prescription change. Electronic circuitry may be included to remotely alert the patient at the time the medication is to be taken via a transmitter and receiver arrangement. The calendar layout of the present invention allows the user to be oriented to the present time and date. This feature may be especially important if the patient is senile or mentally impaired, or on a regimen of multiple medications.

It is contemplated that multiple units may be installed in homes throughout an area, yielding the possibility that a business can burgeon. In particular, a pharmacist, or other licensed medical professional, could initially deliver the unit to the patient's home. At this time, the professional would program the device and fill it with a full month's supply of medication. Thereafter, the professional could return to the patient's home for the purpose of replenishing the medication supply. The professional may refill the unit at the patient's premises from inventory in a mobile medicine van or may return to a central location, where the unit can be filled and returned the following day. Although the unit can be filled by hand, it will often be preferable to use a dispensing robot, particularly where multiple units are refilled at a central collection location.

As can be seen in FIG. 1, top 47 of the dispensing unit mimics a calendar. Top 47 is hinged at pivot point 45 directly in front of a time and date display. The hinge enables the entire top to be lifted at once and pivoted as indicated by arrow 46 so that individual compartments are exposed for loading medications. The pill tray into which the compartments are formed may be unitary and constructed of plastic or any other suitable material. As illustrated, top 47 may be secured by a lock 48 when in the closed position. Typically, the medical professional who will refill the unit will have a key for lock 48, but the patient will not. The key for lock 48 will preferably not be a "master" key for all similar units, but may be a unique key. For example, an electronic "key" encoded with a personal identification number (PIN) such as the patient's social security number may be utilized for this purpose.

A medicine data sheet 51 may be stored adjacent to the dispensing unit, such as in a slot defined in the side. The professional filling the unit can refer to data sheet 51 for important information. This information can include the patient's medicine schedule and types of medicine, as well as contraindications, uses, allergies of the particular patient, and any other special considerations. To reduce the possibility for error, data sheet 51 may include an identifier unique to the particular patient, such as the patient's Social Security number. This same identifier should also be placed somewhere on the unit to facilitate matching. Data sheet 51 may be constructed of paper printed with the above information and covered with a lamination for protection.

In the illustrated construction, the entire dispensing unit is elevated by four legs 52, which may include protective rubber pads 53. A water unit 33 is provided to give the patient a convenient water source for taking medication. In the illustrated construction, water unit 33 is placed in the lower right hand corner of the dispensing unit. Water unit 33 includes a pump 38 and associated hardware, as well as a cup dispenser 62 which issues cups in this case via a knob 61.

The calendar format of the dispenser unit includes a plurality of conceptual dispensing "modules," each corresponding to a single day of the month. As can be seen, the dispenser unit includes four rows of seven daily modules, and one row of three daily modules. This construction yields a total of thirty-two (32) such modules. In other embodiments, such as those not including water dispenser 33 in the illustrated location, thirty-five (35) such modules could be provided. More modules would not be necessary so long as a monthly refill schedule is used.

Figure 2:
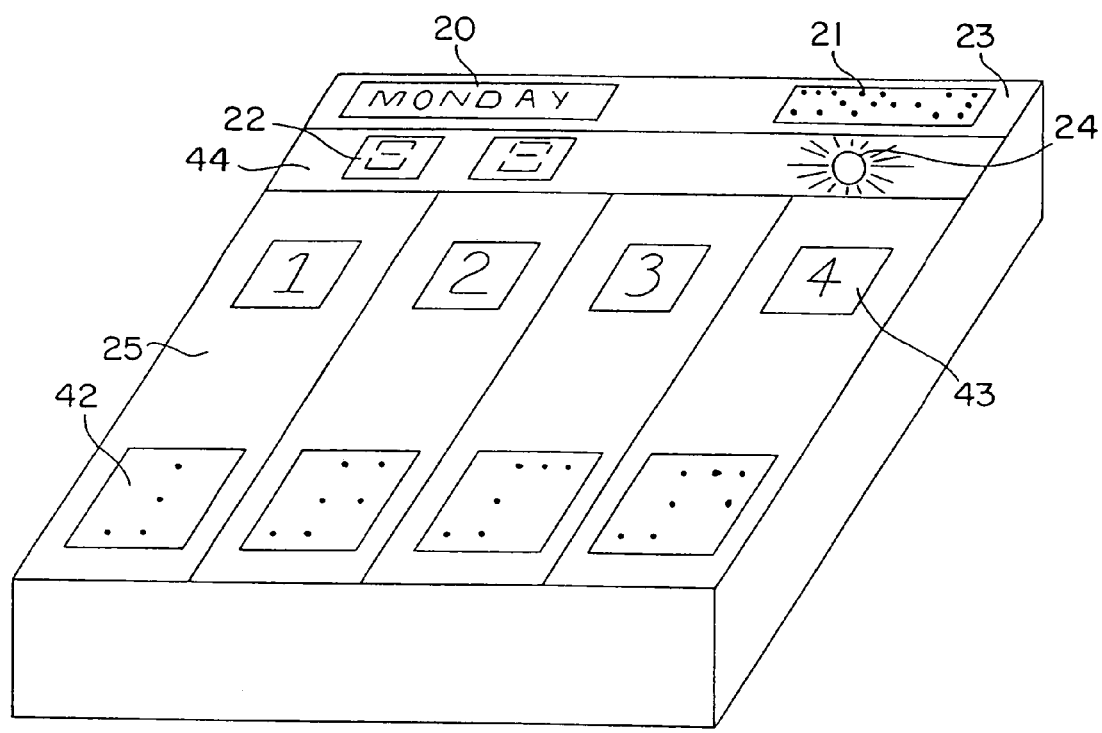
FIG. 2 is a perspective view of an exemplary daily medication dispensing module such as is utilized in the medication dispenser of FIG. 1.

FIG. 2 illustrates an individual dispensing module corresponding to a single day of the week. In particular, a module of the top row in the calendar display is illustrated. As can be seen, the illustrated module includes a total of four (4) separate dispensing compartments or "pill boxes" corresponding to the four doses that many patients must take each day. For example, many medicine regimens require doses at 8:00 AM, 12:00 PM, 4:00 PM and 8:00 PM. Each dispensing compartment will be prefilled with the medication required at the corresponding time.

Being from the top row, the illustrated module includes a representation 20 of the day of the week along with the Braille representation 21 for the day to which the module corresponds. In some embodiments, the printed and Braille indicia may appear on a strip 23 made of paper or plastic slid into place from the side of the unit. Generally, strip 23 will include indicia for the entire week and have a sufficient length to extend across the transverse width of the dispensing unit.

Alternatively, Braille representation 21 may be permanently affixed to the dispensing unit. The representation 20 of the day may be an LED or backlit display to illuminate during that day of the week. This may be especially desirable to help maintain the patient's orientation. Alternatively or in addition, the unit may include a means of audibly informing the patient of the current time and day. This may occur, for example, at the time medicine is retrieved.

Each module also preferably includes a digital display 22 showing the particular date. Display 22 may be constructed of adjacent seven-segment LED displays of the type well known in the art. Display 22 will change automatically according to the programming of the dispensing unit's microprocessor. In other words, the microprocessor, when properly programmed, will "know" the day and date of the week. Display 22 may be continuously lit, or may be lit only when that day of the week is reached.

Figure 6:
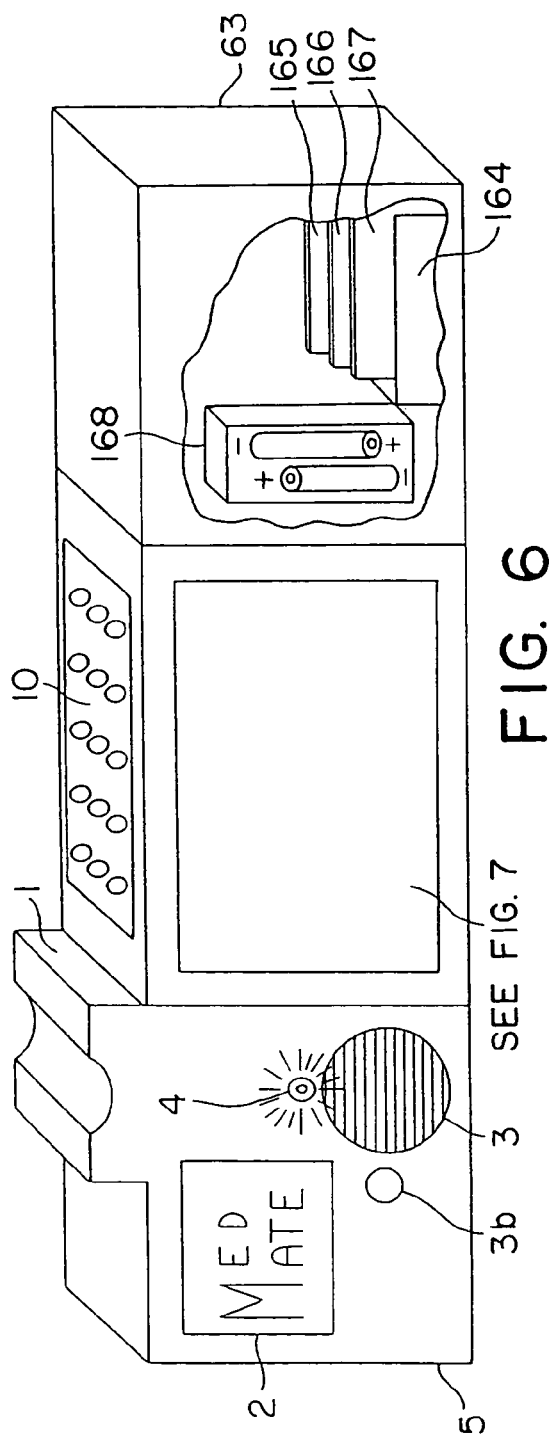
FIG. 6 is a drawing of the audio-visual display utilized in the medication dispenser of FIG. 1.

In addition to display 22, each unit preferably includes an LED alarm indicator 24 that flashes when the internal logic reaches a preset time for dispensing medication. Referring now also to FIG. 6, an audible alarm also issues a warning via speaker 3 at the same time that alarm indicator 24 begins to flash. Both signals continue until the patient responds using a dispensing actuator. At that point, an acknowledgement LED 4 may be illuminated.

Thus, the following three things preferably occur when medication is needed: first, the audible alarm sounds; second, the "take medication" LED 24 flashes; and, third, when the patient responds by using the dispensing actuator, the door 25 of the appropriate dispensing compartment rises so that the contents are easily available. As shown in FIG. 2, the door 25 may include indicia 43 indicating the door number as well as a corresponding Braille representation 42.

While the dispensing actuator may comprise a simple button, presently preferred embodiments utilize an actuator that responds to some unique characteristic of the patient. For example, the illustrated construction utilizes a finger print reader 1 that has been programmed to detect the unique finger print pattern of the patient. Finger print reader 1 may include a small housing defining a longitudinal trough into which the user's finger is inserted for reading. If the correct finger print is detected, the appropriate door 25 will open. If not, all of the doors 25 remain closed.

This feature is advantageous in making the dispensing unit virtually child-proof as well as preventing unauthorized persons, children and adult, from gaining access to the medication. It should be appreciated, however, that the present invention is not limited to finger print readers for this purpose. Where suitable, any of the following technologies may also be utilized for this purpose: a) key, b) key card, c) card with microchip, d) any other card, e) bar-code scan, f) any other scan system, g) eye-gram print, h) any other eye print, i) hand print, j) voice print, k) signals or any other signal print, l) infra-red, m) telephone, n) television, o) solar, p) embedded microchip in person or q) satellite.

Figure 3:
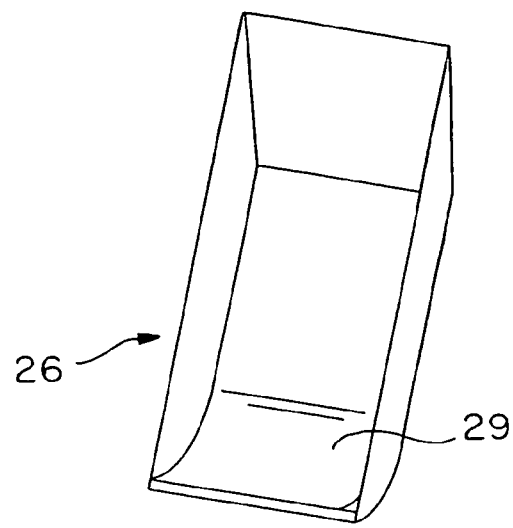
FIG. 3 is a perspective view of an individual medication dispensing compartment from the module of FIG. 2 with the lid removed to illustrate the curved bottom surface on the inside thereof that facilitates pick-up of the medication.

FIG. 3 shows the interior surface of an individual medication dispensing compartment 26. As can be seen, compartment 26 defines a sloped bottom surface 29 that facilitates removal of the medication that would be located inside. Preferably, surface 29 conforms to NASA ergonomic standard 3000 which allows medication to be withdrawn easily. It will be appreciated that the bottom of the unit may be personalized depending on the particular needs of the patient. For example, if a large quantity of medication/food are to be contained in the compartment, it may be deep. Otherwise, the compartment may be shallow or have a medium depth.

Figure 4:
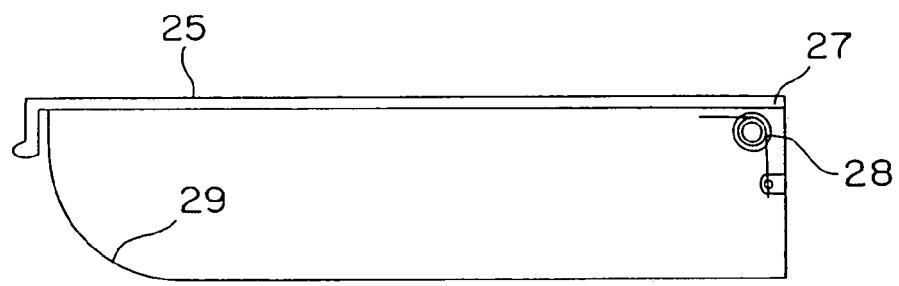
FIG. 4 is a side view of the individual dispensing compartment showing a torsion spring used to urge the lid into an open position.
Figure 5:
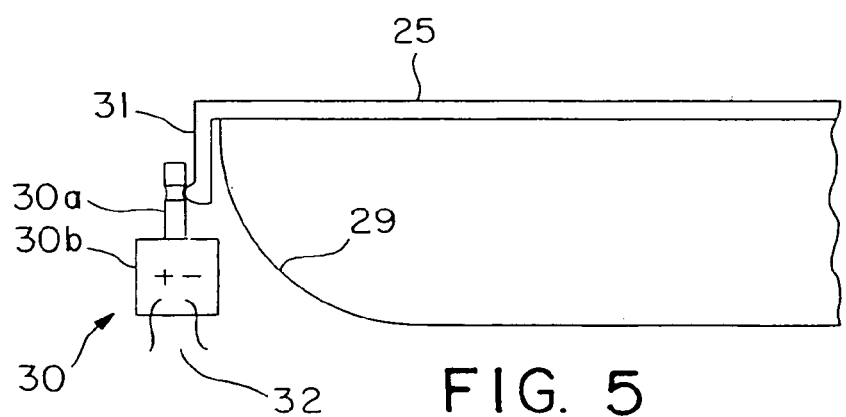
FIG. 5 is a diagrammatic representation of an electromechanical latching mechanism for releasing the compartment lid to an open position.

As can be seen on FIG. 4, door 25 pivots open about a hinge 27. A suitable spring, such as torsion spring 28, urges door 25 into the open position when released. As shown in FIG. 5, a latching mechanism is provided to hold door 25 in the closed position, against the force of spring 28, until medication is to be taken.

In the illustrated embodiment, the latching mechanism includes a molded plastic latch 31 extending from the front portion of the respective door 25. Latch 31 provides a detenting action in the armature 30a of a solenoid device 30. In particular, latch 31 is held in a groove on armature 30a, as illustrated. The detenting force of the latch 31 is greater than the force provided by torsion spring 28, thus normally maintaining door 25 in the closed position.

When the time for medication is reached, and the patient has utilized the dispensing actuator, latch 31 is disengaged. This occurs by actuation of solenoid 30, which draws armature 30a downwards. As a result, latch 31 and armature 30a are uncoupled, at which time torsion spring 28 swings door 25 into the open position. The medicament located in the respective compartment 26 is now exposed so that the user can insert fingers to extract the medication (or an extraction device if fingers do not permit picking up).

Referring again to FIG. 6, sound emanates from speaker 3 at the time medication is to be taken. The sound may be an alarm buzzer or, if the personal-message module (explained more fully below) is installed, something more pleasant and personal. The sound intensity can be adjusted with the volume knob 3b located next to speaker 3. By personalizing the message, the system will also help keep the patient from feelings of isolation and depression. The alert will continue until the dispenser actuator has been utilized. As can be seen, finger print reader 1, speaker 3, volume knob 3b, and acknowledgment LED 4 are all housed within an enclosure 5.

Figure 11B:
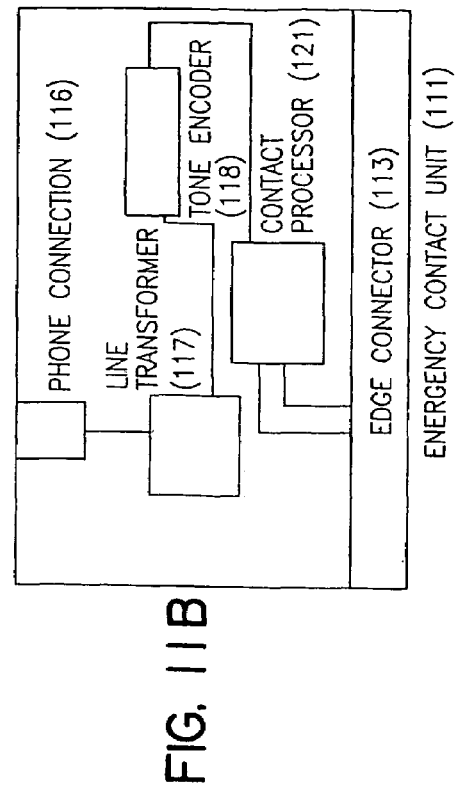
FIGS. 11A-11D diagrammatically illustrate respective add-in card features that may be utilized with the medication dispenser of FIG. 1.
Figure 11D:
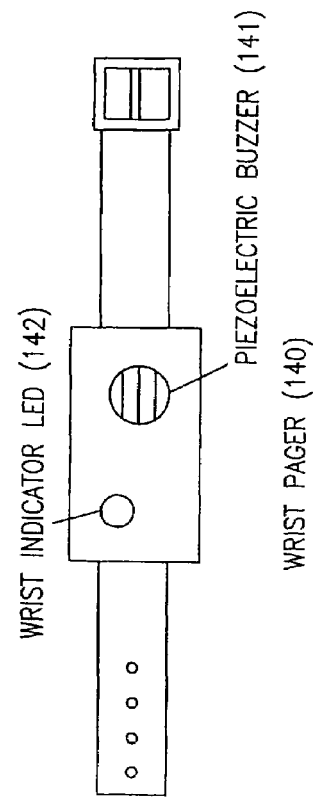
Figure 11A:
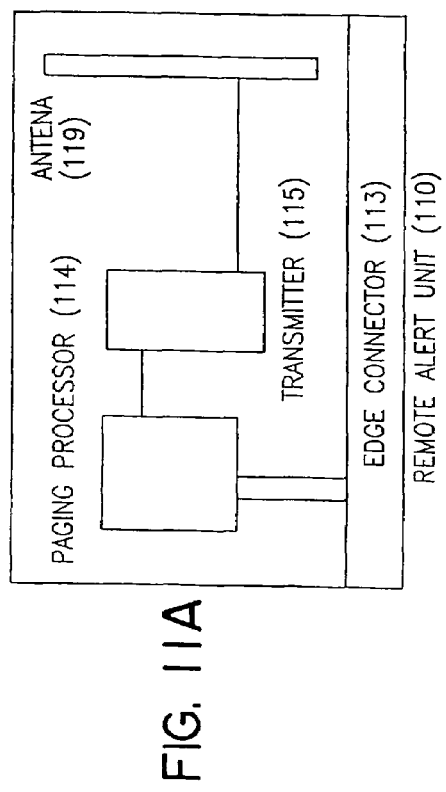
Figure 11C:
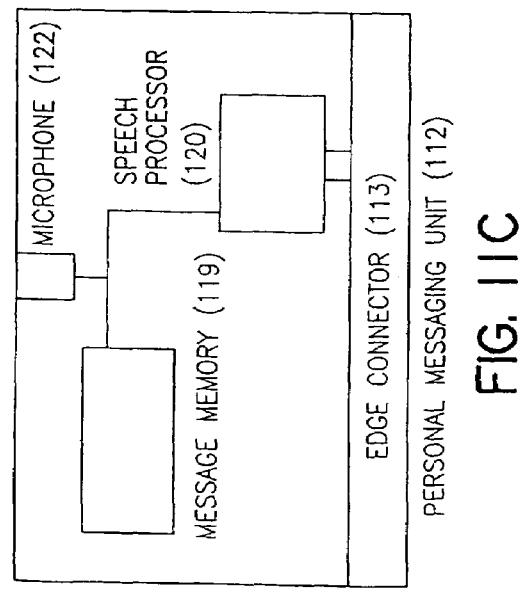

In the illustrated embodiment, housing 5 is positioned to the left of a time and date display. The front of this enclosure may also have a suitable logo, such as "MED-MATE" logo 2. A programming keypad 10 is also provided, which may be housed in the control panel enclosure. A compartment 63 may be located to the right of the time and date display to contain various feature 30 connectors 164-167 which hold electronic cards for additional features. Exemplary feature cards which will be explained more fully below include remote alert or "paging" unit 110 (FIG. 11A), emergency contact unit 111 (FIG. 11B) and personal messaging unit 112 (FIG. 11C).

Normally, the unit is powered by AC provided through power cord 80. A battery-backup unit 168 may also be provided to continue operation of the dispensing apparatus during power outages, or, in the alternative, simply function to preserve the computer memory functions.

Figure 7:
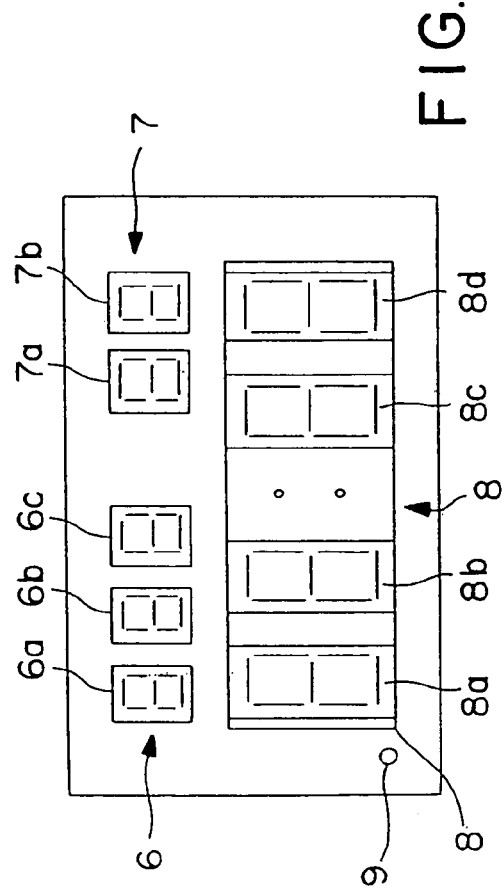
FIG. 7 is an enlarged view showing the time and date display incorporated into the audio-visual display of FIG. 6.

As can be seen most clearly in FIG. 7, the time and date display includes a month indicator 6. In this case, month indicator 6 includes three alphanumeric LED displays 6a, 6b, and 6c to show the month by its common three letter abbreviation. The date indicator 7 comprises a pair of alphanumeric LED displays 7a and 7b. In a similar manner, the time indicator 8 comprises four seven-segment LED displays 8a, 8b, 8c, and 8d. An AM/PM indicator 9 comprises a single LED and is here located to the left of the time and date display.

Figure 8:
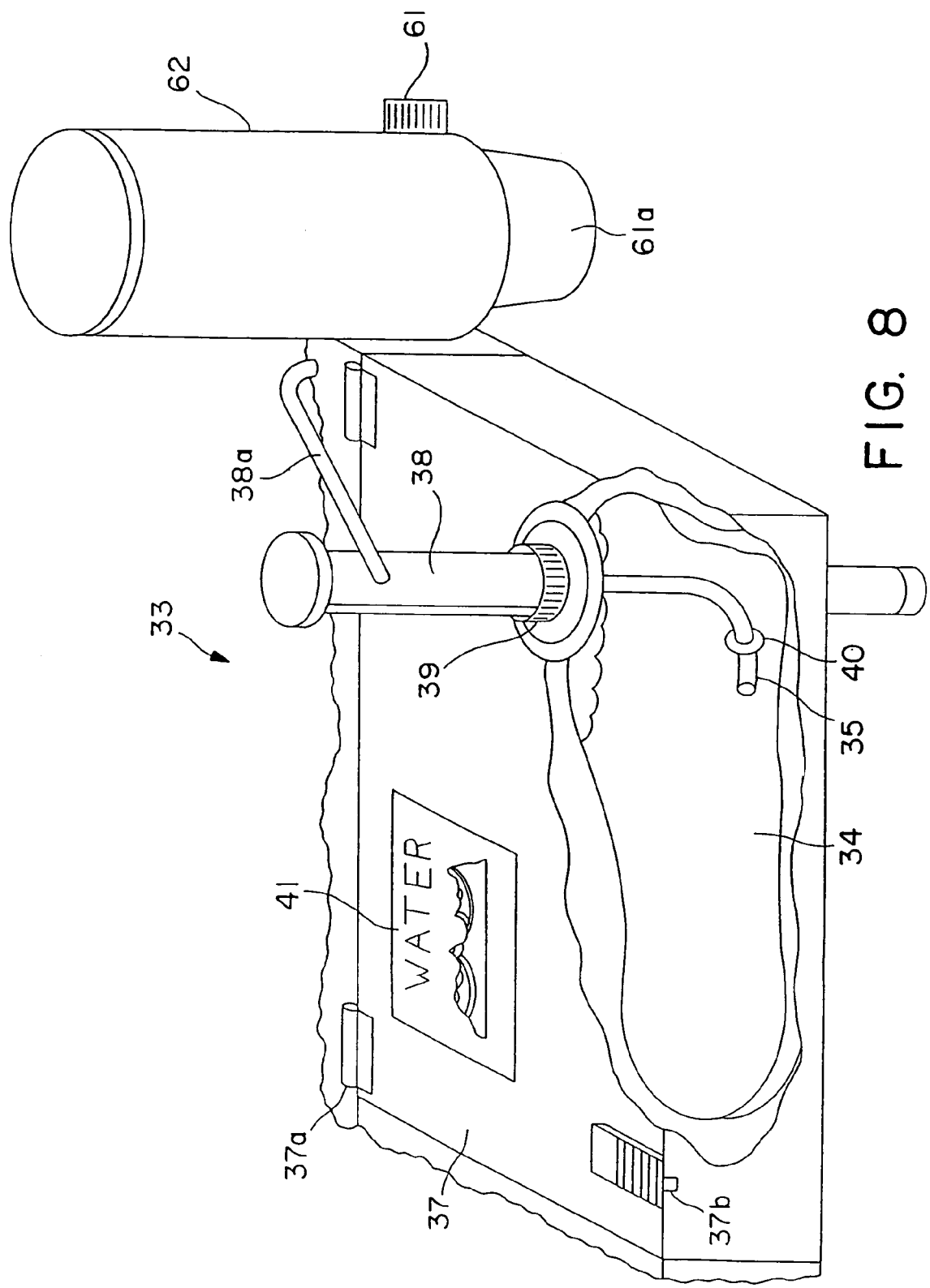
FIG. 8 is an enlarged view with cutaway portions of the water and cup dispensing feature of the medication dispenser of FIG. 1.

FIG. 8 illustrates in greater detail various aspects of water dispenser 33. In this case, the water is contained in a bladder 34 and is drawn upward via the bladder tube 35. Bladder 34 is preferably disposable (e.g., an I.V. fluid bag) such that it can be easily replaced. Bladder 35 and tube 36 are contained below the lid 37 of the water compartment. Lid 37 is hinged at 37a and is normally clasped shut using lid snap latch tab 37b.

Water is pumped out from bladder 34 through a swiveling spout 38a extending from pump 38. Pump 38 may be secured with a locking ring 39 that is a threaded fitting. To ensure moisture does not escape from bladder 34, an annular seal 40 may be placed at the point of connection between bladder 34 and tube 35. The water compartment may be labeled with a logo as indicated at 41. A cup holder 62 may be located on the side of the water dispenser to release cups 61a, such as using a release knob 61.

In an alternative construction, the water can be contained in a jug placed under the dispensing unit. The water would be pumped up from the jug by pump 38 via suitable tubing. An advantage of this arrangement is that the water supply would generally have to be replaced less often. This also eliminates the requirement for a water compartment in the unit itself, allowing more medicine compartments to be provided. Alternatively, the water supply can be connected by tubing to a continuous source of fresh water, such as the water supply coming into the home.

Figure 9:
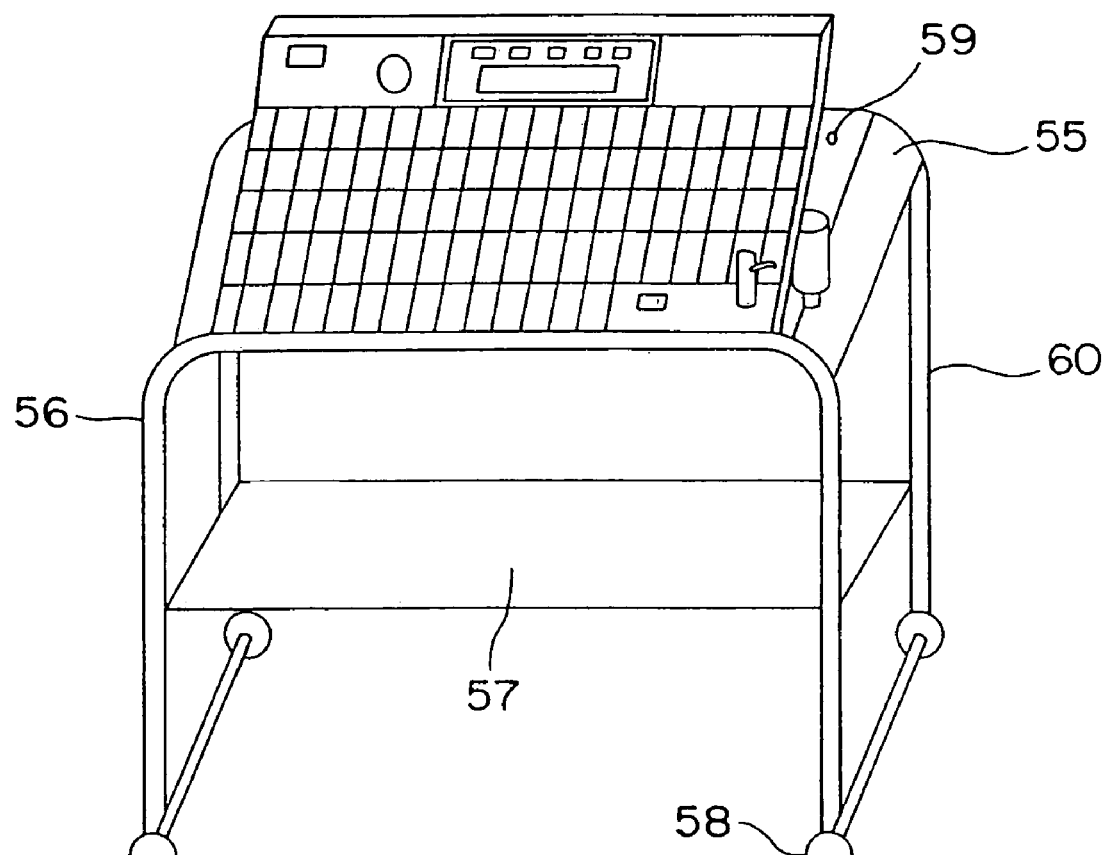
FIG. 9 is a view showing an exemplary transport cart, which may be remote controlled.

Referring now to FIG. 9, the dispensing unit may be placed on a mobile cart 55 in the patient's home. In an exemplary construction, mobile cart 55 may comprise an aluminum frame 56, an extra-use tray 57 for handy storage, and four locking soft-roll wheels 58. Preferably, the four legs 52 of the dispensing unit can register with four holes 59 defined into the top surface of the cart. It may be desirable in many cases to provide cart 55 with a suitable drive motor that can be remotely controlled by the patient.

Figure 10:
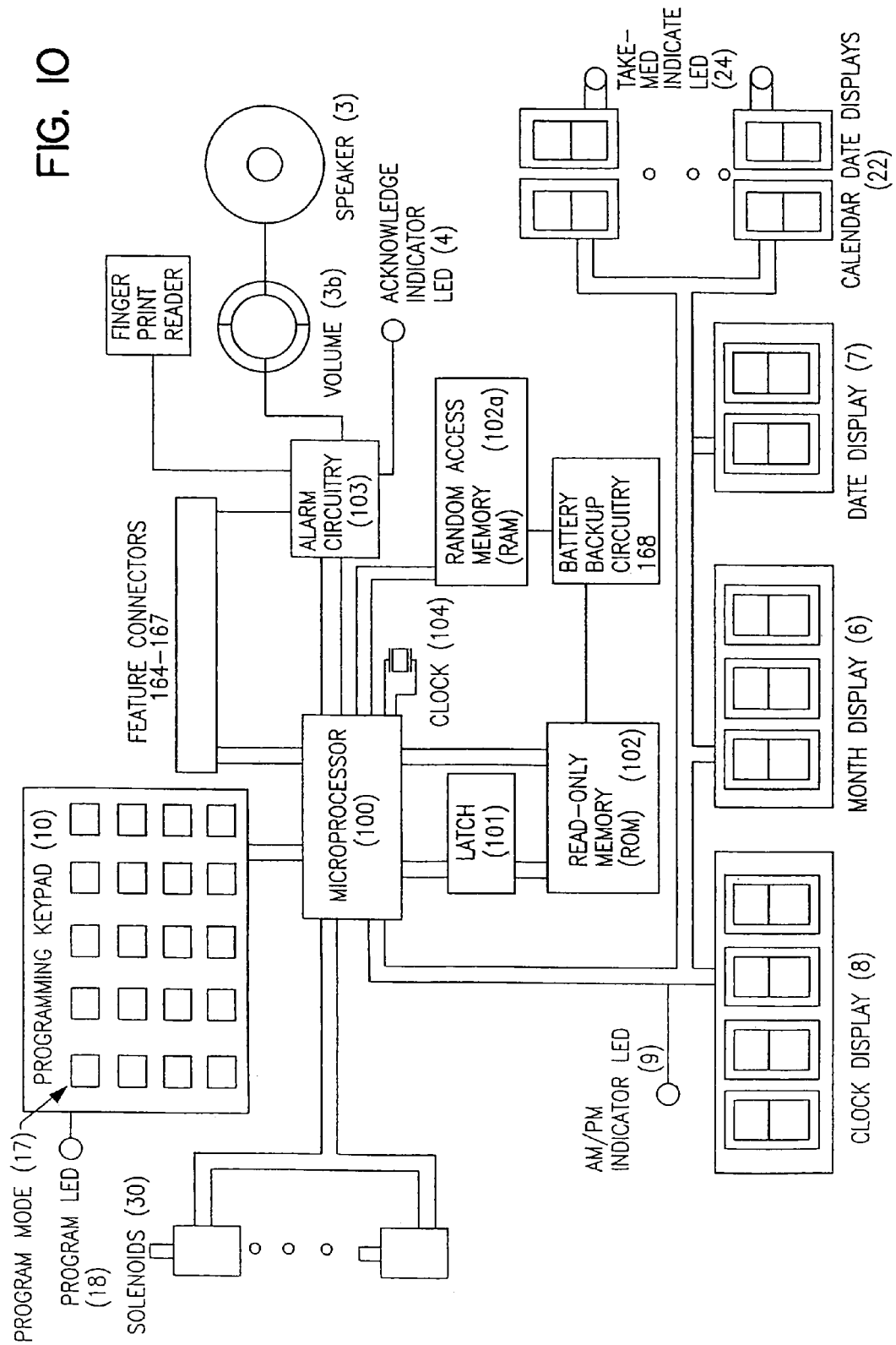
FIG. 10 is a diagrammatic view of preferred electronic circuitry utilized in the medication dispenser of FIG. 1.

FIG. 10 diagrammatically illustrates the layout of preferred electronic circuitry that can be used in the dispensing unit. The circuitry includes an appropriate microprocessor 100, such as a powerful 16-bit controller that may run at 20 MHz or other suitable clock speed regulated by a clock crystal 104. A latch 101 allows memory addressing of Read-Only Memory ("ROM") 102. Memory 102, which for example may have at least 64 Kb of memory space, stores the program required for operation of the device. Memory 102 is preferably of the EPROM type to permit programming changes as necessary, as well as to allow the patient's finger print information to be stored.

Microprocessor 100 is programmed with machine level code in the manner well known in the art and governs the functioning of various aspects of the dispensing unit, such as doors 25, month display 8, date displays 7 and 22, clock display 8, the alarms and acknowledgements. If present, the program also controls remote alert unit 110, emergency contact unit 11, and the personal message unit 112 and other features that may be provided.

The programming keypad 10 is utilized for user-specific programming. Preferably, the keypad is "locked," meaning that it can be programmed only by those who have the proper programming code. In this case, the code must be entered before any alteration of the programming may take place. Once the code has been entered, keypad 110 allows simple programming of the timing of doses, current time and date, and, if present, emergency contact unit 111 and personal messaging unit 112. The data for the timing is stored in a random access memory ("RAM") 102a. RAM 102a is kept active by system power, but, in the event of a power failure, its contents may be maintained by battery-backup circuit 168. This allows the unit to maintain its function for several hours without re-programming.

Microprocessor 100 provides an internal clock to maintain the correct time at all times. The clock display 8 may be updated once per minute, while the date display 7 may be updated once per day at 12:00 A.M. The AM/PM indicator 9 is preferably in the illuminated state during the PM hours and is turned off during the AM hours. The month display 6 and calendar date displays 22 are updated once per month when microprocessor 100 determines a new month has started.

When the internal clock reaches a programmed time, microprocessor 100 signals the alarm circuitry 103 and an audible alert is issued through a speaker 3 (whose volume may be controlled by a volume knob 3b as discussed above). At this time, a take-medicine LED indicator 24 is illuminated on the calendar. The audible and visible indicators are kept in an "ON" condition until the patient's finger is recognized by finger print reader 1. At this time, the acknowledge indicator LED 4 illuminates for a predetermined period of time, e.g. ten seconds, and then returns to the off state. When the patient's finger print is recognized, the appropriate solenoid 30 is energized to release the correct medicine dispensing door 25. The patient is then given access to the medicine located in the medicine compartment.

Various enhanced features will now be described with reference to FIGS. 11A-11D. In particular, FIGS. 11A-C diagrammatically illustrate remote alert unit 110, emergency contact unit 111 and personal messaging unit 112, respectively. A wrist worn pager device 140 for use with remote alert unit 110 is diagrammatically illustrated in FIG. 11D.

If the remote alert unit 110 is added, microprocessor 100 signals the paging processor 114 through the edge connector 113. It will be appreciated that edge connector 113 is connected to feature connector 164 of the dispensing unit. In response to the signal from microprocessor 100, paging processor 114 will have transmitter 115 emit a radio-frequency signal through antenna 119. This signal is then picked-up by a receiver in wrist-pager 140. Although a wrist pager is illustrated, it should be appreciated that other types of pagers, such as belt worn pagers, are included within the scope of the present invention.

When a signal is received from antenna 119, wrist-pager 140 may issue an audible alert, such as by a piezo-electric buzzer 141. A flashing LED 142 or other visual signal may also be provided. In this manner, the patient will be informed to return to the medication dispensing unit to retrieve the medication. When the patient's finger print is recognized by the microprocessor, the alarm indicators on both the dispensing unit and wrist pager 140 are turned off and operation resumes as normal.

If the emergency contact unit 111 is present, operation is similar to that described above, except that response by the patient is required within a preselected time constraint. If the patient's finger print is not recognized within the time constraint, contact processor 121 causes the tone encoder 118 to place a pre-programmed phone number onto the telephone lines. Line transformer 117 and phone connector 116 are provided to facilitate communication between tone encoder 118 and the telephone line.

The time constraint and emergency contact number are user-programmable through programming keypad 10. Emergency contact unit 111 may preferably be programmed with up to three different phone numbers. If no answer is detected after a selected number of rings, e.g. eight rings, the unit can phone the other telephone numbers. When each number is called, microprocessor 100 waits for the selected number of rings before continuing successively to the next number, until a connection is made.

When microprocessor 100 detects an answer on the other end, a message is played, alerting the recipient to a possible problem with the patient. After the message is played, the unit preferably hangs-up. The unit can then wait a predetermined period of time, e.g., sixty seconds, for a call back as a safety feature. If no call back is detected, the unit will call the number cyclically again, with functions repeating as described above. Once the unit has received a call-back verification, it will resume normal operation.

If personal messaging unit 112 is present, the functioning of the medicine dispensing unit will not change except the audible alerts will be a personal voice. Instead of a buzzer-type alarm, microprocessor 100 will direct speech processor 120 to play a message stored in message memory 119 when an alarm is called for. The personal message is recorded by use of the programming keypad and a microphone 122 on the personal messaging unit. In exemplary embodiments, the message may be up to ten seconds in duration and will repeat at three second intervals until the patient has responded using the finger print reader. Operation of the dispensing unit then resumes as normal.

Figure 12:
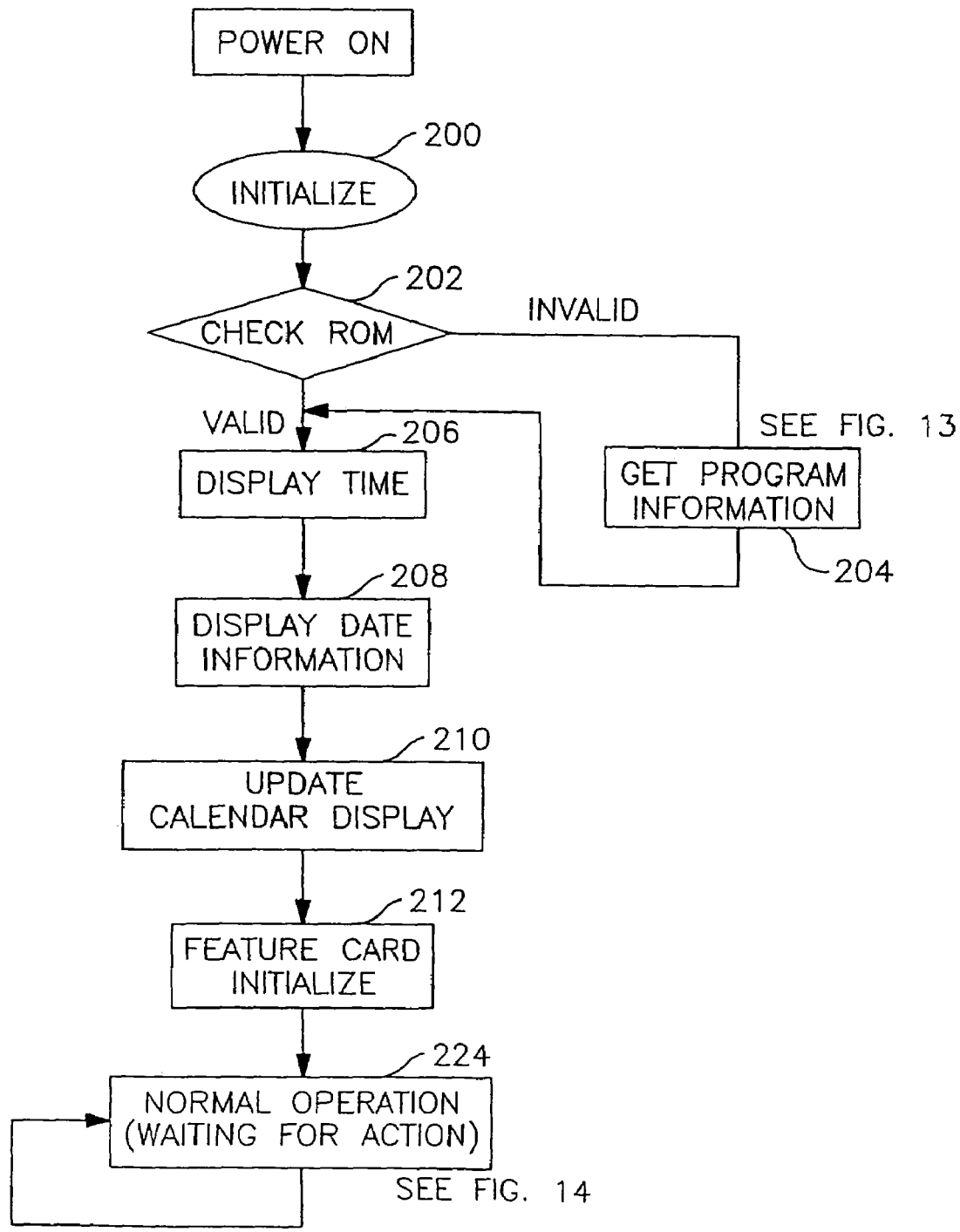
FIG. 12 is a flow chart of preferred logic utilized in the microprocessor of the medication dispenser.
Figure 13:
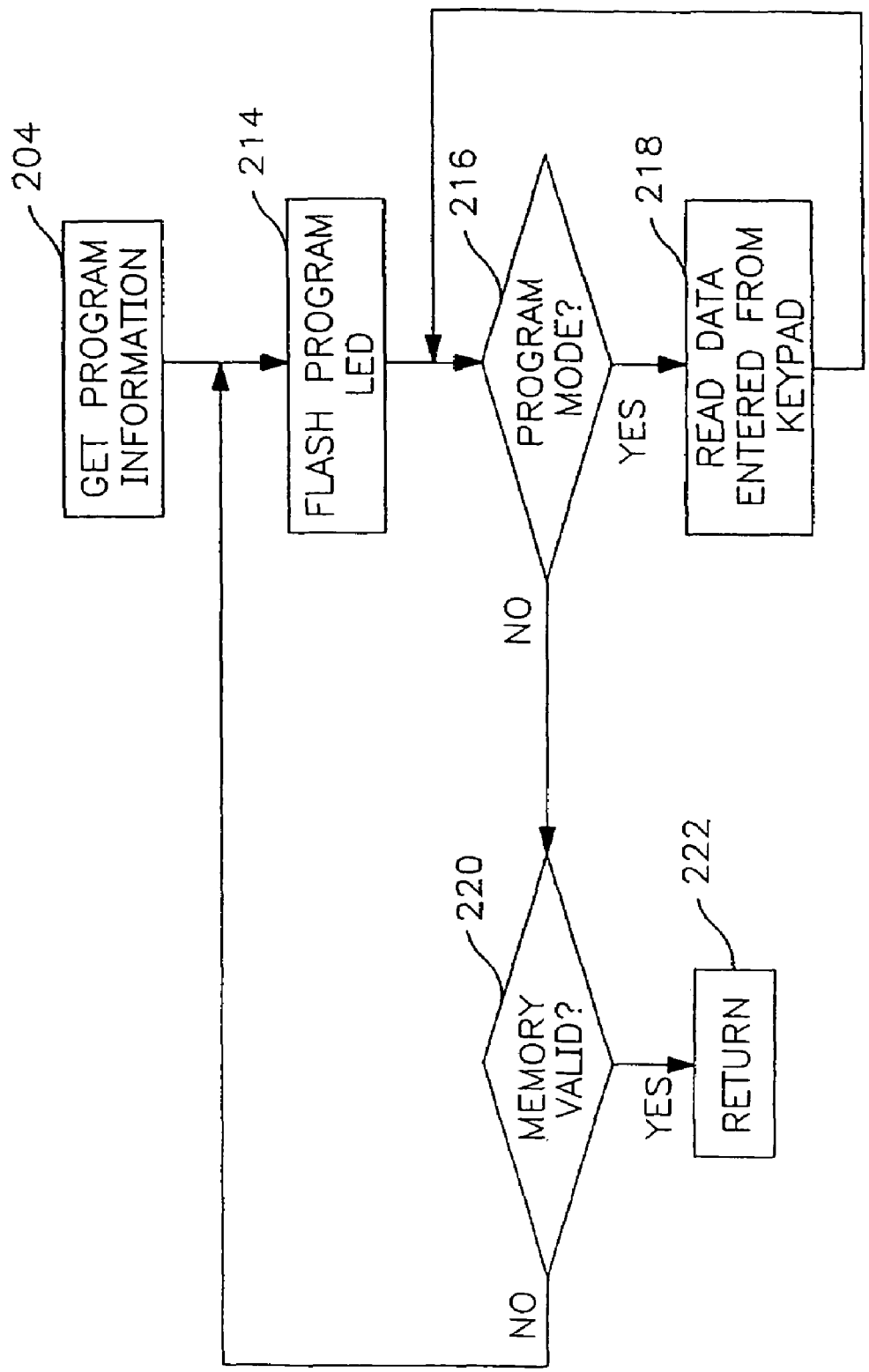
FIG. 13 is a flow chart of preferred logic utilized by the microprocessor for obtaining programming information.

FIGS. 12, 13 and 14 show a preferred logical flow illustrating operation of the dispensing unit. Referring now particularly to FIG. 12, microprocessor 100 initializes itself when system power is applied, as shown at 100. Microprocessor 100 reads from the on-board memory 102, as indicated at 202. Microprocessor 100 checks at 204 to see if programming information is present and whether or not it is valid. If information is valid, microprocessor 100 uses the information to display the current time (at 206), the current date (at 208), the current day and finally it updates the LED's which make up the calendar display (at 210).

Microprocessor 100 then searches the feature card slots at 212 for an installed card. If one or more is found, microprocessor 100 then configures itself to use them at appropriate times. If none are present, microprocessor 100 ignores these slots and uses the built-in audible and visible alerts. If programming is determined to be invalid, then microprocessor 100 will perform the operations shown in FIG. 13.

Referring now particularly to FIG. 13, microprocessor 100 requires programming information and flashes a program LED 18 at 214 associated with programming keypad 10. A program mode button 17 on the programming keypad, which places the microprocessor in a PROGRAM state or a RUN state, must be set to PROGRAM mode in order to enter program information (as shown at 216). An authorized code must be input to allow programming or changes to the programming. Microprocessor 100 will continue to flash LED 18 until valid information has been entered (as shown at 218) and the program mode button has been released from PROGRAM mode back to RUN mode. Once a program has been entered and the program mode button released, a check of memory validity is performed at 220. The operation of the unit returns to normal as shown at 222.

FIG. 14 illustrates operation of the unit under normal circumstances. Normal operation is achieved at 224 when microprocessor 100 has determined that program information in memory 102 is valid and all displays and feature cards have been initialized. At this point, microprocessor 100 continuously checks its internal clock at 226 and 228 for a match with program information in memory 102. If no match occurs, then the time, day, date and calendar displays are updated to reflect their actual current values, as shown at 230. Microprocessor 100 continues in this loop of events until such time as the programmed information and the internal clock of microprocessor 100 match values. At this point, microprocessor 100 turns on the audible and visual alerts, as shown at 232. If remote alert unit 110 and/or personal messaging unit 112 are installed, they function at this time in the manner described above.

When the alerts have been issued, the clock, date, day and calendar displays are all updated to reflect their current values, as shown at 234. Microprocessor 100 then checks for matched from the finger print reader at 236, indicating the patient has responded to the alerts. If a match is found, the acknowledge LED is illuminated at 238 and the solenoid corresponding to the program information is energized at 240. The medicine compartment lid is thus opened and the patient is allowed access to the medicine within.

If no signal is found, microprocessor 100 will continuously update clock information and check for the presence of a match from the finger print reader. At this point, shown between points A and B, if emergency contact unit 111 is installed, contact processor 121 will initialize a countdown timer at 242 with a preprogrammed value. If no patient response is received, i.e., no match from the finger print reader, within the countdown period, then, as indicated at 244, emergency contact unit 111 will perform its actions as described above. When the medicine has been dispensed, as indicated by the acknowledge LED and the energizing of the appropriate solenoid, then the clock, day, date, and calendar are updated and microprocessor 100 continues to check its internal clock against the next programmed time stored in ROM. The medicine dispensing unit will continue in this fashion until such time as the program information changes.

Figure 1A:
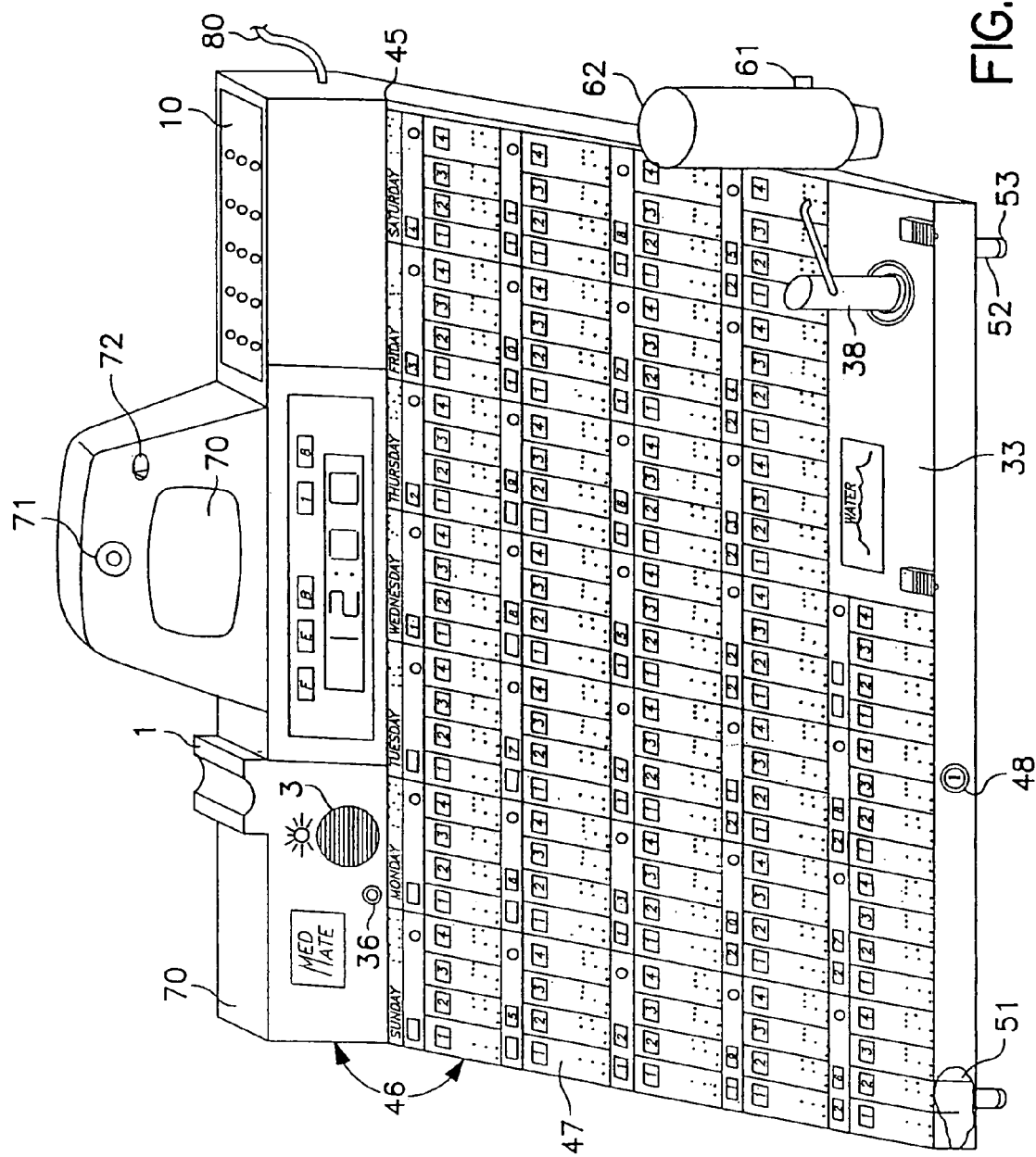
FIG. 1A is a perspective view similar to FIG. 1 of an alternative embodiment.

FIG. 1A illustrates an alternative embodiment that allows two-way communication with a central monitoring facility. In particular, the dispensing unit of FIG. 1A includes a video monitor 70 and video camera 71 for this purpose. In a preferred methodology, two-way communication with the central monitoring facility will be activated if the patient does not utilize finger print reader 1 within a predetermined time after medicine is due to be taken. Audible messages can be provided to the patient through speaker 3. Sounds at the patient's home can be monitored through built-in microphone 72. It should be appreciated that any suitable means of providing this communication may be utilized including wired or wireless technologies. The communication may be audio and video, or either one by itself, and may be one-way (to the monitoring facility), if desired. Information that can be retrieved and transferred includes virtually all types of medical information in an effort to maintain the highest consistent degree of good health possible. This includes lab studies, written information, test results, body imaging and teaching. The ability to write electronic prescriptions (such as by a nurse practitioner) and to access patient charts to add these prescriptions or change/delete these prescriptions in the chart is also contemplated. The unit may have various electronic ports for this purpose as will be recognized by one skilled in the art.

It should be understood that the dispensing unit of the invention can be used in conjunction with or controlled by a computer. For example, the video monitor 70 shown in the unit of FIG. 1A can function as a monitor screen for such a computer. This can permit the patient to engage in various computer-based therapies, such as cognitive therapy regimens, using the dispensing unit, or utilize the dispensing unit for virtually any other purpose for which a computer can be employed.

While presently preferred embodiments of the invention have been shown and described, modifications and variations thereto may be made by those of ordinary skill in the art without departing from the spirit and scope of the present invention. For example, a "time delay/time reset" switch can be included so the patient may be able to go off for the day and put entire machine on "hold" without losing memory. The design may also be adapted for quadrapleqics with the doors opening from underneath instead of on top (medicine falls down into trough, e.g., straw-like apparatus). In addition, it should be understood that aspects of the various embodiments may be interchanged in whole or in part. Furthermore, those of ordinary skill in the art will appreciate that the foregoing description is by way of example only, and is not intended to be limitative of the invention.

What is claimed is:

1. A medicament dispensing apparatus comprising:
a housing having at least one medicine compartment for containing at least one medicament therein;
a release mechanism associated with said at least one medicine compartment to normally prevent access to said medicament and actuatable to selectively allow access thereto;
processor means for calculating a predetermined time at which access to said medicament therein is to be permitted;
a conspicuous indicator responsive to said processor means for alerting a user of said predetermined time;
a dispenser actuator for use by the user after said conspicuous indicator has been activated to indicate that the user is ready to retrieve the medicament, said processor means responsively activating said release mechanism; and
communication means for providing two-communication of information with a central monitoring facility.

2. A medicament dispensing apparatus as set forth in claim 1, wherein said communication means provides at least one of visual and audible communication with the central monitoring facility.

3. A medicament dispensing apparatus as set forth in claim 2, wherein said communication means includes a video monitor and a video camera.

4. A medicament dispensing apparatus as set forth in claim 1, wherein said video monitor is further operative to function as a computer monitor.

5. A medicament dispensing apparatus as set forth in claim 1, wherein said communication means includes an on-board microphone.

6. A medicament dispensing apparatus as set forth in claim 1, wherein said processor is adapted to activate said communication means if said dispenser actuator is not activated by a user within a selected period of time.

7. A medicament dispensing system as set forth in claim 1, wherein said housing has a planar surface arranged in a calendar format.

8. A medicament dispensing apparatus as set forth in claim 1, wherein said dispenser actuator functions to read user-specific information.

9. A medicament dispensing apparatus as set forth in claim 8, wherein said dispenser actuator functions to read a unique physical characteristic of a user.

10. A medicament dispensing apparatus as set forth in claim 9, wherein said dispenser actuator comprises a finger print reader.

11. A medicament dispensing apparatus as set forth in claim 1, wherein said conspicuous indicator includes an on-board transmitter operative to deliver a signal to a portable receiver carried by the user.

12. A medicament dispensing apparatus as set forth in claim 11, wherein said portable receiver comprises a portable pager unit.

13. A medicament dispensing apparatus as set forth in claim 1, wherein said housing includes at least one electronic port located thereon.

14. A medicament dispensing apparatus as set forth in claim 13, wherein said electronic port allows exchange of electronic information with said processor means.

* * * * *